(12) United States Patent
Aberdam et al.

(10) Patent No.: US 9,085,754 B2
(45) Date of Patent: Jul. 21, 2015

(54) ISOLATED POPULATION OF CELLS AND METHODS OF GENERATING AND USING SAME

(75) Inventors: Daniel Aberdam, Nice (FR); Edith Aberdam, Nice (FR); Efrat Barak, Nofit-Doar-Na HaAmakim (IL); Michal Amit, Misgav (IL); Joseph Itskovitz-Eldor, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 1211 days.

(21) Appl. No.: 12/450,515

(22) PCT Filed: Mar. 27, 2008

(86) PCT No.: PCT/IL2008/000435
§ 371 (c)(1),
(2), (4) Date: May 5, 2010

(87) PCT Pub. No.: WO2008/120201
PCT Pub. Date: Oct. 9, 2008

(65) Prior Publication Data
US 2010/0233136 A1 Sep. 16, 2010

Related U.S. Application Data

(60) Provisional application No. 60/907,363, filed on Mar. 29, 2007.

(51) Int. Cl.
C12N 5/00 (2006.01)
C12N 5/077 (2010.01)
C12N 5/073 (2010.01)

(52) U.S. Cl.
CPC ........ *C12N 5/0603* (2013.01); *C12N 2501/155* (2013.01); *C12N 2501/40* (2013.01); *C12N 2501/60* (2013.01); *C12N 2502/1394* (2013.01); *C12N 2506/02* (2013.01); *C12N 2510/00* (2013.01)

(58) Field of Classification Search
None
See application file for complete search history.

(56) References Cited

U.S. PATENT DOCUMENTS

| | | |
|---|---|---|
| 2003/0027331 A1 | 2/2003 | Yan et al. |
| 2004/0197310 A1 | 10/2004 | Sanberg et al. |
| 2004/0234997 A1 | 11/2004 | Li et al. |

FOREIGN PATENT DOCUMENTS

| | | |
|---|---|---|
| EP | 1452594 | 9/2004 |
| WO | WO 02/097068 | 12/2002 |
| WO | WO 2006/040763 | 4/2006 |
| WO | WO 2008/120201 | 10/2008 |

OTHER PUBLICATIONS

Nomaguchi et al (Exp Hemat 29: 850-855, 2001).*
Schulz et al (BMC Neurosci 4: 1-13, 2003).*
Conner, DA (Current Protocols in Mol Biol 23.2.1-23.2.7, 2000).*
Communication Pursuant to Article 94(3) EPC Dated Jan. 24, 2011 From the European Patent Office Re. Application No. 08720058.0.
Invitation to Pay Additional Fees Dated Jul. 30, 2008 From the international Searching Authority Re.: Application No. PCT/IL08/00435.
International Search Report Dated Oct. 10, 2008 From the International Searching Authority Re.: Application No. PCT/IL08/00435.
International Preliminary Report on Patentability Dated Dec. 30, 2009 From the International Bureau of WIPO Re.: Application No. PCT/IL2008/000435.
Written Opinion Dated Oct. 10, 2008 From the International Searching Authority Re.: Application No. PCT/IL08/00435.
Aberdam et al. "Key Role of P63 in BMP-4-Induced Epidermal Commitment of Embryonic Stem Cells", Cell Cycle, 6(3): 291-294, Feb. 1, 2007. p. 291, § 2, p. 292, § 3, Fig.1.
Halder et al. "Induction of Ectopic Eyes by Targeted Expression of the Eyeless Gene in *Drosophila*", Science, 267: 1788-1792, Mar. 24, 1995. Fig.5.
Supplementary European Search Report and the European Search Opinion Dated Jun. 7, 2010 From the European Patent Office Re. Application No. 08720058.0.
Aberdam "Epidermal Stem Cell Fate: What Can We Learn From Embryonic Stem Cells?", Cell and Tissue Research, XP019564047, 331(1): 103-107, Sep. 6, 2007.
Aberdam et al. "A Multipotent Ectodermal Cell Population Derived From Human Embryonic Stem Cells for Skin and Cornea Cell Therapy", Journal of Investigative Dermatology, XP009133641, 127(Suppl.2): S63 (377) [Oral 011], Oct. 2007. & 37th Annual Meeting of the European Society for Dermatological Research, Zurich, Switzerland, Sep. 5-8, 2007.
Aberdam et al. "A Pure Population of Ectodermal Cells Derived From Human Embryonic Stem Cells", Stem Cells, XP002510251, 26(2): 440-444, Feb. 1, 2008.
Aberdam et al. "Embryonic Stem Cells as A Cellular Model for Neuroectodermal Commitment and Skin Formation", Comptes Rendues—Biologies, XP022152812, 330(6-7): 479-484, Jul. 13, 2007.
Gambaro et al. "BMP-4 Induces a Smad-Dependent Apoptotic Cell Death of Mouse Embryonic Stem Cell-Derived Neural Precursors", Cell Death and Differentiation, XP002582528, 13(7): 1075-1087, Jul. 2006. Abstract.
Iuchi et al "Immortalized Keratinocyte Lines Derived From Human Embryonic Stem Cells", Proc. Natl. Acad. Sci. USA, XP002415686, 103(6): 1792-1797, Feb. 1, 2006. Abstract, p. 1792.
Ji et al. "Generation and Differentiation of Human Embryonic Stem Cell-Derived Keratinocyte Precursors", Tissue Engineering, XP002415687, 12(4): 665-679, Apr. 1, 2006. Abstract.
Metallo et al. "Directed Differentiation of Human Embryonic Stem Cells to Epidermal Progenitors", Methods in Molecular Biology, XP001525208, 585(Chap.7): 83-92, 2010. Abstract.
Metallo et al. "Retinoic Acid and Bone Morphogenetic Protein Signaling Synergize to Efficiently Direct Epithelial Differentiation of Human Embryonic Stem Cells", Stem Cells, XP009110662, 26(2): 372-380, Feb. 1, 2008. Abstract.
Xu et al. "BMP4 Initiates Human Embryonic Stem Cell Differentiation to Trophoblast", Nature Biotechnology, XP002323561, 20(12): 1261-1264, Dec. 1, 2002. Abstract.

*Primary Examiner* — Daniel E Kolker
*Assistant Examiner* — Aditi Dutt

(57) ABSTRACT

An isolated homogeneous population of cells comprising a plurality of human ectodermal progenitor cells. Also provided are methods of generating and using the population of cells.

9 Claims, 4 Drawing Sheets

(56) References Cited

OTHER PUBLICATIONS

Communication Pursuant to Rules 70(2) and 70a(2) EOC Dated Jun. 24, 2010 From the European Patent Office Re. Application No. 08720058.0.

Response Dated May 12, 2011 to Communication Pursuant to Rules 70(2) and 70a(2) EPC of Jun. 24, 2010 From the European Patent Office Re. Application No. 08720058.0.

Response Dated Dec. 13, 2010 to Communication Pursuant to Rules 70(2) and 70a(2) EPC of Jun. 24, 2010 From the European Patent Office Re. Application No. 08720058.0.

Communication Under Rule 71(3) EPC Dated Mar. 13, 2013 From the European Patent Office Re. Application No. 08720058.0.

Communication Pursuant to Article 94(3) EPC Dated Sep. 13, 2012 From the European Patent Office Re. Application No. 08720058.0.

Chung et al. "Human Embryonic Stem Cell Lines Generated Without Embryo Destruction", Cell Stem Cell, XP002604696, 2(2): 113-117, Feb. 7, 2008.

* cited by examiner

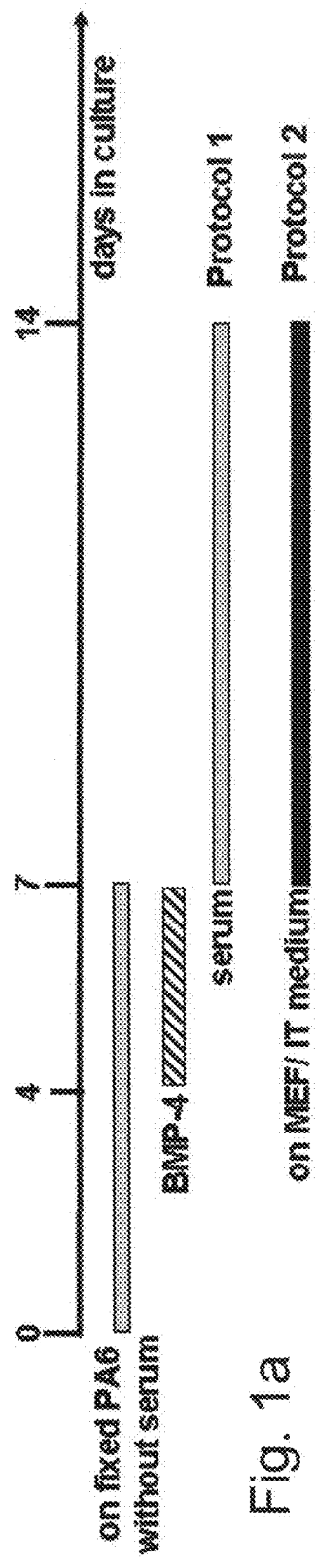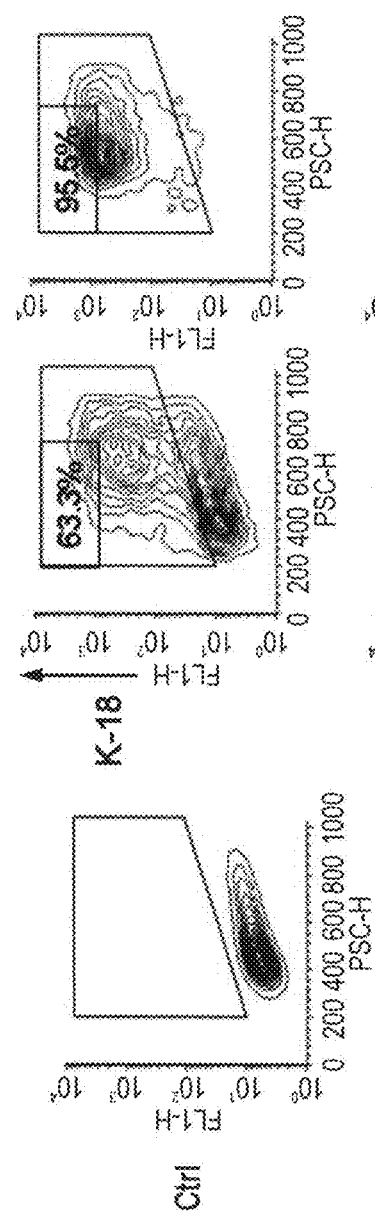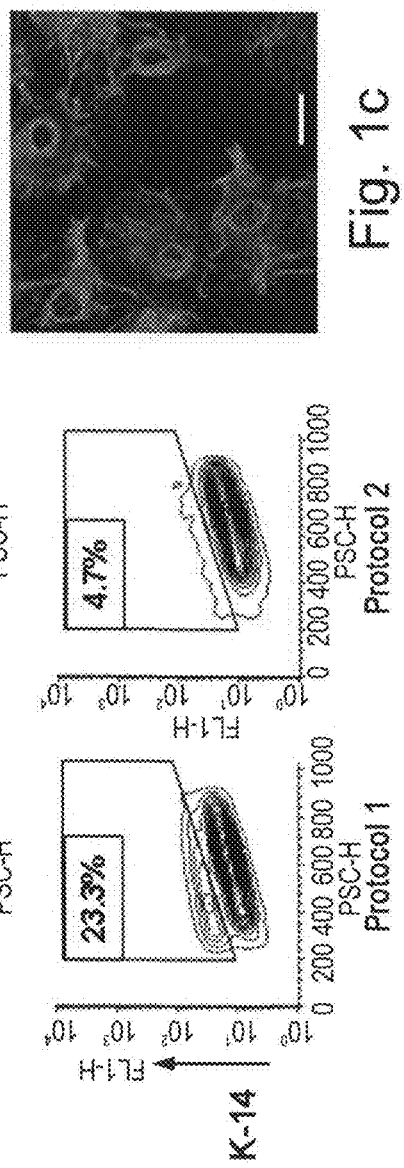
Fig. 1a
Fig. 1b
Fig. 1c

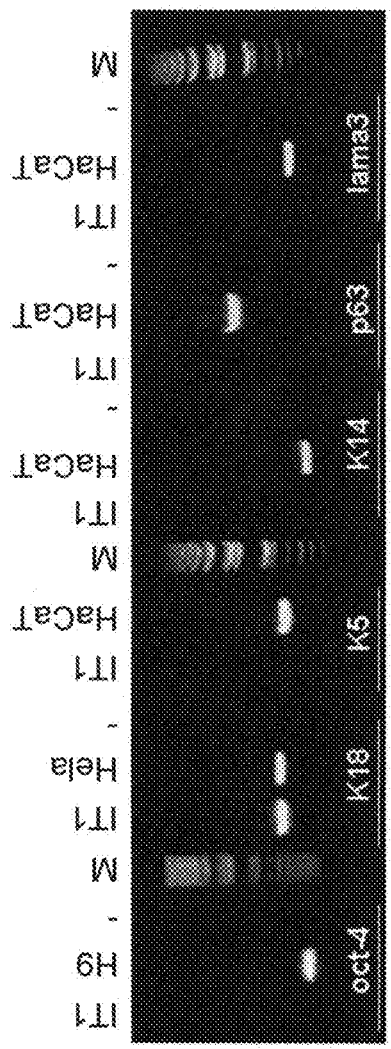
Fig. 2a
Fig. 2b
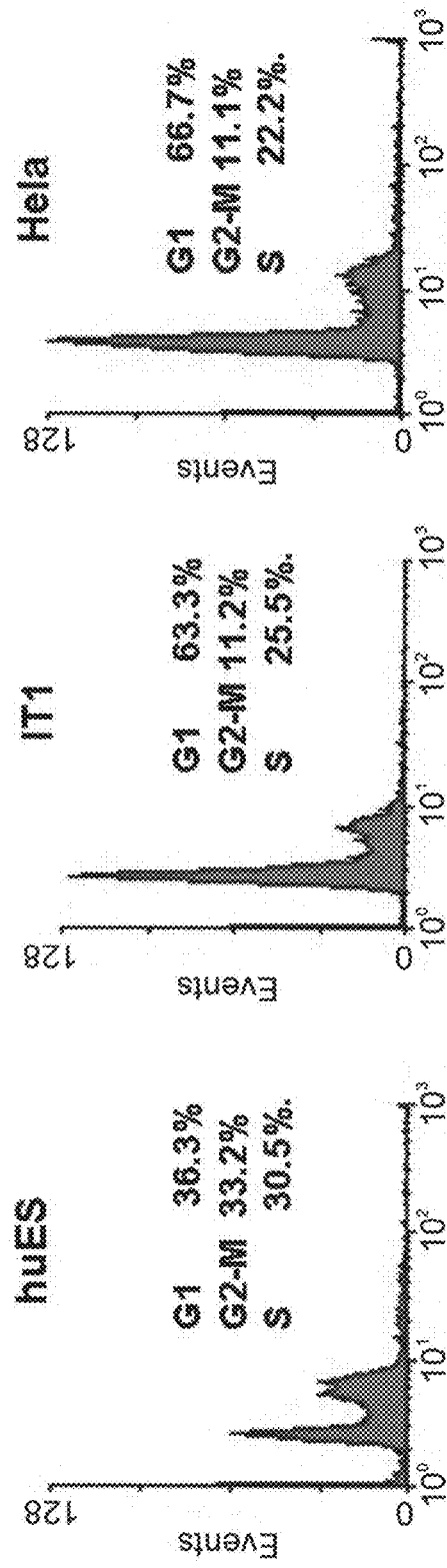
Fig. 2c

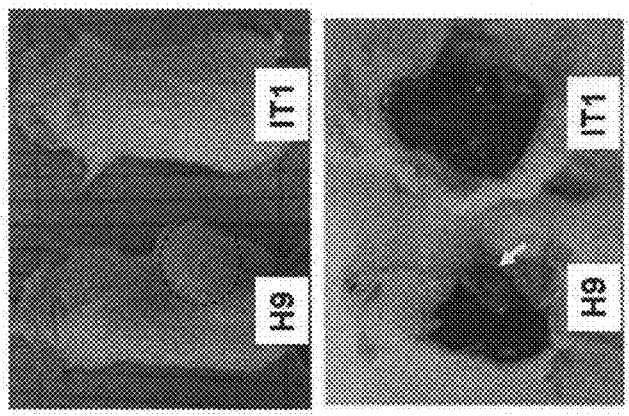
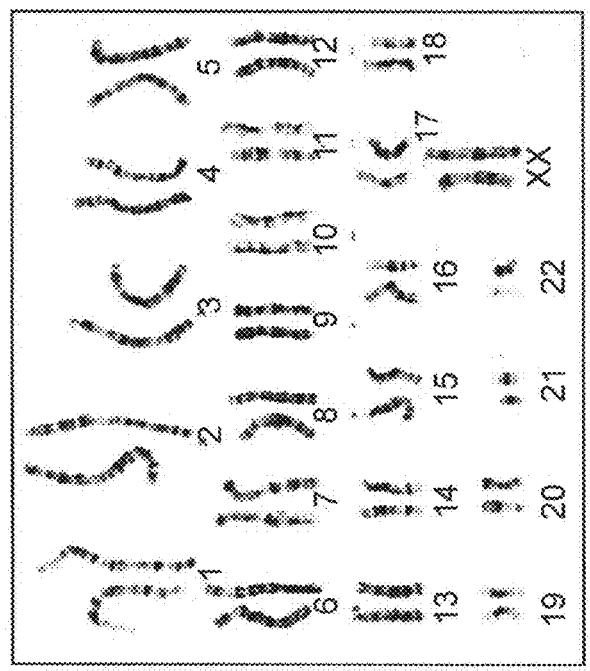
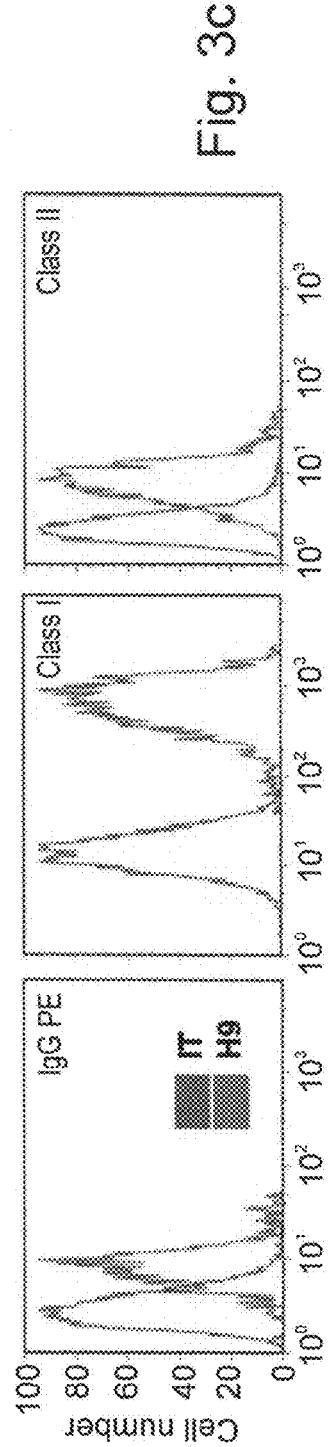
Fig. 3a
Fig. 3b
Fig. 3c

SEQUENCE LISTING

```
<160> NUMBER OF SEQ ID NOS: 22

<210> SEQ ID NO 1
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 1
gagaacaatg agaaccttca ggaga                                          25

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
ttctggcgcc ggttacagaa cca                                            23

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
gccacagtac acgaacctgg                                                20

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
tcgaaactgt gcgggcctgg g                                              21

<210> SEQ ID NO 5
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 5
catcgatgac cagcttctg                                                 19

<210> SEQ ID NO 6
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 6
```

```
catcgatgac cagcttctg                                          19

<210> SEQ ID NO 7
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 7
tagatgcccc caaatctca                                          19

<210> SEQ ID NO 8
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 8
gtccaaggca tcaccaag                                           18

<210> SEQ ID NO 9
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 9
atgattggca gcgtggag                                           18

<210> SEQ ID NO 10
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 10
gtccagctgt gaagtgctt                                          19

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
gaccattgag gacctgagga                                         20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
catacttggt gcggaagtca                                         20

<210> SEQ ID NO 13
<211> LENGTH: 20
<212> TYPE: DNA
```

```
<213> ORGANISM: Artificial sequence
<220> FEATURE:
<223> OTHER INFORMATION: Single strand DNA oligonucleotide

<400> SEQUENCE: 13
ccacatcgct cagacaccat                                               20

<210> SEQ ID NO 14
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 14
tgaccaggcg cccaat                                                   16

<210> SEQ ID NO 15
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 15
tgaagcccag cgcatga                                                  17

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16 ccctttatc agcttctgct t                                              21

<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 17
tttcccaccc cgagatga                                                 18

<210> SEQ ID NO 18
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 18
tgcggcgagc atccat                                                   16

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
acctggctag cgaaaagcaa                                               20
```

```
<210> SEQ ID NO 20
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 20
cccgttcaac atccttagtt tatca                                              25

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
acctggctag cgaaaagcaa                                                    20

<210> SEQ ID NO 22
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 22
cccgttcaac atccttagtt tatca                                              25
```

ISOLATED POPULATION OF CELLS AND METHODS OF GENERATING AND USING SAME

RELATED APPLICATIONS

This Application is a National Phase of PCT Patent Application No. PCT/IL2008/000435 having International filing date of Mar. 27, 2008, which claims the benefit of U.S. Provisional Patent Application No. 60/907,363 filed on Mar. 29, 2007. The contents of the above Applications are all incorporated herein by reference.

FIELD AND BACKGROUND OF THE INVENTION

The present invention, in some embodiments thereof, relates to isolated populations of cells and methods of generating and using same.

Human embryonic stem cells (hUES) have the ability to differentiate into various cell lineages in vitro and in vivo including but not limited to melanocytes, hematopoietic cells, hepatocytes, kidney cells, skeletal muscle cells, dopaminergic neurons, glial cells, cardiomyocytes, endothelial cells, and osteoblasts. hESCs cells are therapeutically attractive because of this pluripotency. The use of such cells and their differentiated progeny is contemplated for the treatment of various conditions. Thus, while huES cells provide a potential cellular source for tissue engineering application, a major limitation resides in the heterogeneity of the committed cell population. The absence of known tissue-specific stem cell surface marker usually prevents cell sorting of the desired cell type, retaining thus contaminated undifferentiated huES which can still produce teratoma. Among the different cell types that can be generated from ES cells, ectodermal cells are of particular interest since they represent the precursors of many epithelial tissues and organs. Although previous studies have reported epithelial differentiation of murine and human ES cells, the heterogeneity of the cell culture impairs the evaluation of homogenous differentiated cell population for cell therapy.

RELATED ART

Bagutti C, Hutter C, Chiquet-Ehrismann R et al. Dermal fibroblast-derived growth factors restore the ability of beta (1) integrin-deficient embryonal stem cells to differentiate into keratinocytes. Dev Biol 2001; 231: 321-333.

Coraux C, Hilmi C, Rouleau M et al. Reconstituted skin from murine embryonic stem cells. Curr Biol 2003; 13: 849-853.

Kawasaki H, Mizuseki K, Nishikawa S et al. Induction of midbrain dopaminergic neurons from ES cells by stromal cell-derived inducing activity. Neuron 2000; 28: 31-40.

Ji L, Allen-Hoffmann B L, de Pablo J J et al. Generation and differentiation of human embryonic stem cell-derived keratinocyte precursors. Tissue Eng 2006; 12: 665-679.

Schuldiner M, Yanuka O, Itskovitz-Eldor J et al. Effects of eight growth factors on the differentiation of cells derived from human embryonic stem cells. Proc Natl Acad Sci USA 2000; 97: 11307-11312.

Troy T C, Turksen K: Commitment of embryonic stem cells to an epidermal cell fate and differentiation in vitro. Dev Dyn 2005; 232: 293-300.

Gambaro K, Aberdam E, Virolle T et al. BMP-4 induces a Smad-dependent apoptotic cell death of mouse embryonic stem cell-derived neural precursors. Cell Death Differ 2006; 13: 1075-1087.

Green H, Easley K, Iuchi S. Marker succession during the development of keratinocytes from cultured human embryonic stem cells. Proc Natl Acad Sci USA 2003; 100: 15625-15630.

Metallo C, Ji L, de Pablo J J, Palecek S P. Retinoic acid and bone morphogenetic protein signaling synergize to efficiently direct epithelial differentiation of human embryonic stem cells. Stem Cells. 2008 February; 26(2):372-80.

SUMMARY OF THE INVENTION

According to an aspect of some embodiments of the present invention there is provided an isolated homogeneous population of cells comprising a plurality of human ectodermal progenitor cells.

According to some embodiments of the invention, the isolated population of cells has a detectable expression of K8 and K18, as determined by RT-PCR.

According to some embodiments of the invention, the isolated population of cells has a normal karyotype.

According to some embodiments of the invention, the isolated population of cells is sustainable in a proliferative state for at least 15 passages.

According to some embodiments of the invention, the isolated population of cells does not exhibit a detectable expression of a marker selected from the group consisting of p63, lama3, k5, k4 and/or Oct-4, as determined by RT-PCR.

According to some embodiments of the invention, the isolated population of cells is able to differentiate into keratinocytes, pluristratified epidermis and cornea.

According to some embodiments of the invention, the isolated population of cells is incapable of producing teratomas in nude mice.

According to some embodiments of the invention, the isolated population of cells is non-immortalized.

According to some embodiments of the invention, the isolated population of cells has a doubling time of about 48 hours in culture.

According to an aspect of some embodiments of the present invention there is provided a method of producing a homogeneous population of human progenitor ectodermal cells, the method comprising:

(a) culturing human ES cells on a stromal feeder layer in serum free medium comprising BMP-4 so as to obtain a heterogeneous population of cells comprising the human ectodermal progenitor cells;

(b) culturing the heterogeneous population of cells in medium comprising a serum on a fibroblast feeder layer to thereby produce the homogeneous population of human progenitor ectodermal cells.

According to some embodiments of the invention, the stromal feeder layer is formaldehyde fixed.

According to some embodiments of the invention, the step (a) is effected for about 7 days comprising:

(i) culturing the human ES cells on the stromal feeder layer in the serum free medium from day 1 to day 4; and (ii) culturing the ES cells on the stromal feeder layer in the serum free medium in a presence of the BMP-4 from day 4 to day 7.

According to some embodiments of the invention, step (b) is effected from day 7 to day 16.

According to an aspect of some embodiments of the present invention there is provided a method of inducing ectodermal lineage differentiation, the method comprising subjecting the population of cells to a treatment which results in ectodermal lineage differentiation.

According to some embodiments of the invention, the treatment comprises genetic modification of the ectodermal progenitor cells.

According to some embodiments of the invention, the genetic modification comprises exogenous expression of ΔNp63 and the ectodermal lineage differentiation is towards epidermis.

According to some embodiments of the invention, the genetic modification comprises exogenous expression of pax-6 and the ectodermal lineage differentiation is towards cornea.

According to some embodiments of the invention, the treatment comprises culturing the ectodermal progenitor cells on extracellular matrix.

According to an aspect of some embodiments of the present invention there is to provided a method of determining an effect of a factor on ectodermal differentiation, the method comprising:

(a) obtaining a homogeneous population of ectodermal progenitor cells;

(b) exposing the population of ectodermal progenitor cells to the factor; and (c) determining an effect of the factor on the population of ectodermal progenitor cells to thereby determine the effect thereof on ectodermal development.

According to some embodiments of the invention, step (a) is effected as described above.

According to an aspect of some embodiments of the present invention there is provided a method of relieving or preventing a medical condition in a subject in need thereof, the method comprising:

(a) obtaining a homogeneous population of ectodermal progenitor cells; and (b) administering the ectodermal progenitor cells into the subject, thereby alleviating the medical condition.

According to an aspect of some embodiments of the present invention there is provided an isolated corneal cell obtained according to the above method.

According to an aspect of some embodiments of the present invention there is provided an isolated epithelial cell obtained according to the above method.

According to an aspect of some embodiments of the present invention there is provided a pharmaceutical composition comprising the cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C depict ectodermal commitment of human embryonic stem cells and isolation of the IT1 cell line. FIG. 1A schematically shows the differentiation protocol for ectodermal commitment. The medium, feeders and range of duration for each stage are shown. Formaldehyde-fixed PA6 stromal cell line was used as feeder; FIG. 1B shows flow cytometry analysis of K18 or K14 expressing cells at day 14 with IgG isotype control or anti-K18 or anti K14 specific antibodies; FIG. 1C shows immunofluorescent analysis of IT1 with anti K18 antibody at passage 6 showing the homogeneity of the IT1 cell population. Scale bar=20 μm. Abbreviations: BMP—bone morphogenic protein; Ctrl—Control; MEF—mouse embryonic fibroblasts.

FIGS. 2A-C characterize the IT1 population. FIG. 2A is a bright phase image of IT1 at confluence; FIG. 2B is a micrograph showing reverse transcription-polymerase chain reaction analysis of total RNA extracted from IT1, undifferentiated hues (H9 cell line), HaCaT and HeLa cells with primers specific for Oct-4, K18, K5, K14, ΔNp63 and lama3 genes, M=size marker; FIG. 2C shows comparative cell cycle kinetics of IT1, H9 and HeLa cells.

FIGS. 3A-C show differentiation characteristics of IT1 cells. FIG. 1A is a karyotype analysis of IT1 as passage 13; FIG. 3B provide photomicrographs showing tumors at week 10 following injection onto SCID mice of IT1 (right) as compared to H9 (left); FIG. 3C is a flow cytometry analysis of MHC class 1 and class II cells in It and H9 cells.

FIG. 4A shows immunofluorescence staining if IT1 cells with anti p63 (green) and anti-k14 (red. Upper panel). No staining was observed when IT1 cells were infected with pax-6 lentivirus as control (lower panel). FIG. 4B shows real time PCR analysis for keratinocyte-specific lama3 and k14 genes and control pax-6 gene. The value for each point was normalized to tomato infected IT1 control cells. The data represents the mean±SEM from three experiments. FIG. 4C shows immunofluorescence of IT1 cells induced to differentiate to keratinocytes when deposited on HaCaT-derived extracellular matrix for 4 days. K18 staining is shown in green and K14 staining is shown in red.

DESCRIPTION OF EMBODIMENTS OF THE INVENTION

Figure 4A:
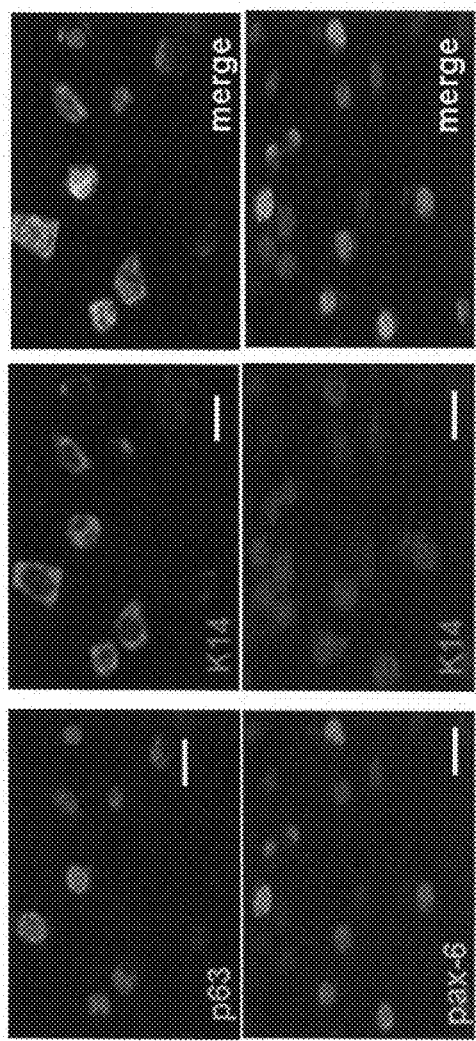
FIGS. 4A-C show differentiation of IT cells into keratinocytes. IT 1 cells expressing exogenous ΔNp63 differentiated into keratinocyte-like cells. IT1 cells were transiently infected with p63 or control lentiviruses for 72 hours and analyzed by immunofluorescence staining and real-time RT-PCR.

The present invention, in some embodiments thereof, relates to isolated homogeneous populations of human ectodermal progenitor cells and, more particularly, but not exclusively, to methods of generating such cells and use of same in research and clinic.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Whilst reducing the present invention to practice, the present inventors uncovered a novel protocol for ectodermal commitment of human embryonic stem cells. The use of this protocol results is homogeneous cell populations which can be used without further selection and screening, as in vitro models to recapitulate early events during embryonic epithelial lineage specification, as well as a source of committed homogeneous cells in clinical trials for (neuro)ectoderm loss.

As is illustrated hereinbelow and in the Examples section which follow, the present inventors were able to reproducibly isolate homogeneous ectodermal cell populations from human ES cells. These cells remain homogeneous following 15 passages (FIG. 1B) and expand up to 60 population doublings. The cells highly resemble somatic cells, showing normal karyotype (see FIG. 3A) and somatic cell cycle kinetics (see FIG. 2C) and do not produce teratomas in nude mice (see FIG. 3B). The cells are able to differentiate into epidermal cells (see FIGS. 4A-C) and nervous cells, supporting their use in research and clinic.

Thus, according to one aspect of the present invention there is provided an isolated homogeneous population of cells comprising a plurality of human ectodermal progenitor cells.

As used herein the term "isolated" refers to cells which are isolated from their natural environment e.g., the human body, embryoid body. In certain embodiments the term relates to a single cell culture.

As used herein the term "homogeneous" refers to a cell culture whereby substantially (>about 95%, 95.5%, 96%, 96.5%, 97%, 97.5%, 98%, 98.5%, 99%, even 100%) all the cells are of the same level and lineage of differentiation. As described herein, such a homogeneous population is preferably obtained by culturing (naïve, non-genetically modified) which negates the need for further steps of selection, such as by using gene-therapy-based selection or antibody-assisted purification.

As used herein the phrase "ectodermal progenitor cells" refers to multipotent cells which are committed to an ectodermal lineage but are not terminally differentiated. Ectodermal progenitor cells of the present invention express, in some embodiments, K18 (GenBank Accession Numbers NM_000224.2, NM_199187.1) and K8 (GenBank Accession Number NM031170), but not K14 (GenBank Accession Number NM016958), K5 (GenBank Accession Number NM000424), p63 (GenBank Accession Number NM003722), lama3 (GenBank Accession Number EF444992), Oct-4 (GenBank Accession Number NM002701) and can give rise to any ectodermal cell or tissue including external ectoderm derived cells (e.g., epidermal, corneal cells, mammary glands, teeth) and endoderm-derived cells (e.g., thymus, pancreas).

The skin comprises an ectoderm-derived epithelial tissue, the epidermis, and a mesoderm-derived connective tissue, the dermis. The epidermal cell is defined as an epithelial cell which constitutes the epidermis. The epidermis comprises a keratinized stratified squamous epithelium comprising, from the dermis towards the outer surface, stratum basale, stratum spinosum, stratum granulosum, stratum lucidum and stratum corneum. The epidermal cell is classified by the cell morphology and expression mode of keratin filaments as indexes. Since keratins 8 and 18 are expressed at the early stage of development, they are used as markers of an epithelial cell at the early fetal period (R. G. Oshima et al., Dev. Bio., 99, 447 (1983)). Keratin 19 is used as a marker of an epithelial cell in a fetus (P. C. Stasiak & E. B. Lane, Nucleic Acids Res., 15, 10058 (1987)). Keratins 5 and 14 are used as a marker of an epithelial cell which constitutes the stratum basale of epidermis (E. Fuchs & H. Green, Cell, 19, 1033 (1980)).

Thus, surface/external ectoderm includes but is not limited to the following cells, structures and tissues, i.e., pluristratified epidermis, epidermis of the skin, including glands, hair and nails (keratinocytes), epithelium of the mouth and nasal cavity, as well as salivary glands, enamel, epithelial of pineal and pituitary glands, lens and cornea and apical ectodermal ridge.

Neuroectoderm includes neural crest and neural tube. Neural crest cells, structures and tissues include, but are not limited to, pigment cells of the skin, ganglia of the autonomic nervous system, dorsal root ganglia, Schwann cells, facial cartilage, spiral septum of developing heart, ciliary body of the eye, adrenal medulla.

Neural tube cells, structures and tissues include, but are not limited to, brain (rhombencephalon, mesencephalon and prosencephalon), spinal cord and motor neurons, retina and posterior pituitary.

In an exemplary embodiment of this aspect of the present invention, the isolated population of cells exhibits a normal karyotype (i.e., 2n human chromosomes). Karyotypic analysis is effected using methods which are well known in the art and described in the Examples section which follows (see FIG. 3a).

In other exemplary embodiments of this aspect of the present invention, the isolated population of cells is sustainable in culture for at least 12, 13, 14, 15, 16 or even 17 passages, after which cells may continue to proliferate or go into senescence. The sustainability in culture and the homogeneity (purity) of the culture suggest that the population of cells of the present invention are of a cell-line like phenotype, which in certain embodiments does not necessitate active immortalization such as by genetic modification [e.g., by expressing a telomerase gene in the cells (Wei, W. et al., 2003. Mol Cell Biol. 23: 2859-2870) or co-culturing the cells with NIH 3T3 hph-HOX11 retroviral producer cells (Hawley, R. G. et al., 1994. Oncogene 9: 1-12)].

In other exemplary embodiments of this aspect of the present invention, the isolated population of cells is incapable of forming teratomas in nude mice (see FIG. 3b), exhibit a somatic cell cycle kinetics (see FIG. 2c) and doubling time (e.g., about 48 hours), supporting its clinical use.

The population of cells of the present invention can be generated such as described in the Examples section which follows.

Thus, according to another aspect of the present invention there is provided a method of producing a homogeneous population of human progenitor ectodermal cells, the method comprising:

(a) culturing human embryonic stem cells on a stromal feeder layer in serum free medium comprising BMP-4 (GenBank Accession Number: NM_007554) so as to obtain a heterogeneous population of cells comprising the human ectodermal progenitor cells;

(b) culturing the heterogeneous population of cells in medium comprising a serum on a fibroblast feeder layer to thereby produce the homogeneous population of human progenitor ectodermal cells.

The phrase "embryonic stem cells" or "ES cells" refers to embryonic cells of human or primate origin, which are capable of differentiating into cells of all three embryonic germ layers (i.e., endoderm, ectoderm and mesoderm). The phrase "embryonic stem cells" may comprise cells which are obtained from the embryonic tissue formed after gestation (e.g., blastocyst) before implantation (i.e., a preimplantation blastocyst), extended blastocyst cells (EBCs) which are obtained from a post-implantation/pre-gastrulation stage blastocyst (see WO2006/040763 to the present inventors] and embryonic germ (EG) cells which are obtained from the genital tissue of a fetus any time during gestation, preferably before 10 weeks of gestation.

The embryonic stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used with this aspect of the present invention. Human ES cells can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03 and TE32.

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter desegregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

It will be appreciated that stem cells in an undifferentiated state are of a distinct morphology, which is clearly distinguishable by the skilled in the art from that of differentiated cells of embryo or adult origin. Typically, undifferentiated stem cells have high nuclear/cytoplasmic ratios, prominent nucleoli and compact colony formation with poorly discernable cell junctions.

It will be appreciated, that embryonic like-stem cells, i.e., those obtained by de-differentiation of adult somatic cells using methods known in the art and are endowed with pluripotency (I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872) can also be used as a source of stem cells in accordance with the teachings of the present invention.

Regardless of the method employed, once stem cells are at hand they are cultured on a feeder layer, preferably a stromal feeder layer, in serum- (or serum replacement-) free medium for about 7 days.

Generally, stem cells are cultured in adherent conditions such as on feeder (e.g., fibroblasts) cells or in feeder-layer free culturing conditions employing a matrix instead of a feeder cell layer.

As used herein, the term "matrix" refers to any substance to which the stem cells can adhere and which therefore can substitute the cell attachment function of feeder cells. Such a matrix typically comprises extracellular components to which the stem cells can attach.

Particularly suitable for use with the present invention are extracellular matrix components derived from basement membrane or extracellular matrix components that form part of adhesion molecule receptor-ligand couplings. Non-limiting examples of suitable matrices which can be used by the method of this aspect of the present invention include Matrigel® (Becton Dickinson, USA), laminin, fibronectin, proteoglycan, entactin, heparan sulfate, and the like, alone or in various combinations. In cases where complete animal-free culturing conditions are desired, the matrix is preferably derived from a human source or synthesized using recombinant techniques. Such matrices include, for example, human-derived fibronectin, recombinant fibronectin, human-derived laminin, foreskin fibroblast matrix or a synthetic fibronectin matrix which can be obtained from Sigma, St. Louis, Mo., USA or can be produced using known recombinant DNA technology.

Thus, in a particular embodiment the cells are cultured on stromal feeder layer, such as described in the Examples section which follows.

Following about 4 days in culture, the medium is supplemented with BMP-4. Culturing with BMP-4 preferably takes place from day 4 to day 7. Monitoring cell differentiation such as by marker expression can be done at any stage of the culture, such as described in details in the Examples section which follows.

In order to render the heterogeneous population (comprising ectodermal progenitors and ectodermal cells) obtained in the first step homogeneous, cells are cultured in a medium comprising serum (or serum replacement) on a fibroblast feeder layer from about day 7 to day 16 of the culture.

It will be appreciated that while the use of serum which is derived from either an animal source (e.g., bovine serum) or a human source (human serum) is limited by the significant variations in serum components between individuals and the risk of having xeno contaminants (in case of an animal serum is used), the use of the more defined composition such as the currently available Serum Replacement™ (Gibco-Invitrogen Corporation, Grand Island, N.Y. USA) may be contemplated.

Thus, culturing reagents (e.g., medium, serum, feeder) are selected according to the intended use. Thus, for example, for clinical use, cells are preferably prepared under xeno-free conditions.

Ectodermal progenitor cells can be differentiated to any ectodermal-derived cells, tissues or structures as outlined hereinabove.

Culturing conditions may comprise genetic modification of the cells (see Examples section which follows) and/or exposure to growth factors.

The following provides exemplary differentiation conditions which can be exploited to direct the differentiation to a particular cell, tissue or structure of interest.

Thus, for example, differentiation into keratinocytes can be effected by exogenous expression of ΔNp63 (GenBank Accession Number NM003722) in the progenitor cells of the present invention. p63 is a member of the p53 family which has been shown to be essential for the development of the epidermis and its derivative in vertebrates. Differentiation of K8/K18+ ectodermal cells into K5/K14+ keratinocytes was demonstrated by Aberdam et al. 2007 Cell Cycle 6:291-294, which is hereby incorporated by reference.

Genetic modification of the ectodermal progenitor cells of the present invention can be effected using methods and constructs which are well known in the art, and described in length in the Examples section.

Another approach for inducing epidermal differentiation involves seeding of the progenitor cells on keratinocyte-derived extracellular matrix as follows: keratinocytes, either Normal Human Keratinocytes (NHK) or HacaT cells a natural immortalized keratinocyte cell line (Available from the ATCC), are seeded at a density of 30,000 cells per $cm^2$ and grown to high confluence (5 to 6 days). The cells are then detached by 15 minutes treatment with 10 mM EDTA in PBS. The flasks or plates are briefly washed with sterile distilled water to eliminate any eventual remaining keratinocytes. The ectodermal progenitors are then seeded on the extracellular matrix and cultured in ectodermal progenitors medium [60% DMEM+30% Ham-F12+10% FCS (FCII Hyclone)+5 □g/ml insulin+0.5 □g/ml hydrocortisone+10 ng/ml EGF]. Alternatively, ectodermal progenitors medium conditioned by keratinocytes is produced as follows: keratinocytes are cultured in ectodermal progenitor medium, from 50 to 100% confluence. Medium is collected every two days, pooled and filtered through a 0.2 □m filtration membrane. Similarly, differentiation may be achieved by replacing the keratinocytes with mesenchymal cells such as fibroblasts.

Differentiation of ectodermal progenitors may also be achieved in in co-culture such as on, Mitomycined (8 □g/ml mitomycin C for 2 hours) keratinocytes (NHK or HacaT) or fibroblasts (40 000 cells/$cm^2$).

The present inventors have demonstrated that seeding of ectodermal progenitor cells on collagen IV (from human placenta, SIGMA), 5 □g/cm2 for about 7 days, results in cells having epithelial-like morphology (cuboids, packed cells), which express de novo beta-catenin, E-cadherin and integrin beta4. The cells loose K8/K18 markers and become K3/K12+ cells, cytokeratins specific of corneal-like cells.

Corneal like cells expressing specific K3-K12 cytokeratins can also be obtained by culture of ectodermal progenitors on ECM produced by corneal fibroblast (COF) or a human corneal cell line (HCE-T, Riken) in ectodermal progenitor medium regular or conditioned by COF or HCE. Differentiation protocol of ectodermal progenitors consist also in co-culture on mitomycined HCE or corneal fibroblasts.

Differentiation of ectodermal progenitors can also be achieved by over expression of Pax 6, a transcription factor known to be essential for in vivo corneal formation (Halder et al, Science 267:1788-1792, 1995), such as by retroviral infection and selection with an antibiotic (blasticidin 5 mg/ml) of the expressing cells. K12/K3 positive cells appear after two weeks of differentiation.

The present inventors have also differentiated the ectodermal progenitors of the present invention into sebocyte-like cells on ECM produced by sebocytes (human sebocyte cell line SZ95, Zouboulis et al, J. Invest. Dermatol. 113:1011-1020, 1999) in medium containing $10^{-7}$ M retinoic acid and 0.5 □M BRL (activator of PPAR□) or in coculture with these cells (not shown). This results in the appearance of sebocyte-specific markers like MCR5 (melanocortin receptor of type 5), SCD-3 (stearoyl-coenzyme A desaturase 3) or cytokeratin K20.

The cells may also be differentiated into insulin-producing cells such as by exogenous expression of the transcription factor Pdx1 known to be essential to pancreatic commitment.

It will be appreciated that in certain embodiments complex macroscopic tissue architecture may also be mimicked in vitro by seeding the progenitors of the present invention on a scaffold.

As used herein, the term "scaffold" refers to a 3 dimensional matrix upon which cells may be cultured (i.e., survive and preferably proliferate for a predetermined time period).

The scaffold may be made uniformly of a single polymer, co-polymer or blend thereof. Both the choice of polymer and the ratio of polymers in a co-polymer may be adjusted to optimize the stiffness of the scaffold. The molecular weight and cross-link density of the scaffold may also be regulated to control both the mechanical properties of the scaffold and the degradation rate (for degradable scaffolds). The mechanical properties may also be optimized to mimic those of the tissue such as at an implantation site. Scaffold material may comprise natural or synthetic organic polymers that can be gelled, or polymerized or solidified (e.g., by aggregation, coagulation, hydrophobic interactions, or cross-linking) into a 3-D open-lattice structure that entraps water or other molecules, e.g., to form a hydrogel. Structural scaffold materials may comprise a single polymer or a mixture of two or more polymers in a single composition. Additionally, two or more structural scaffold materials may be co-deposited so as to form a polymeric mixture at the site of deposition. Polymers used in scaffold material compositions may be biocompatible, biodegradable and/or bioerodible and may act as adhesive substrates for cells. In exemplary embodiments, structural scaffold materials are easy to process into complex shapes and have a rigidity and mechanical strength suitable to maintain the desired shape under in vivo conditions.

Living ectoderm tissue prepared by the method of the present invention can be used for regenerative therapy in any case where de novo formation or implantation of ectodermal tissue is beneficial. The ectodermal progenitor cells can be transplanted per se (without the fear of teratoma formation) or can be differentiated ex vivo followed by implantation.

Thus, according to yet another aspect of the present invention, there is provided a method of relieving or preventing a medical condition in a subject in need thereof, the method comprising: obtaining a homogeneous population of ectodermal progenitor cells; and administering the ectodermal progenitor cells into the subject, thereby alleviating the medical condition.

Thus, ectodermal tissue may be implanted into fetal, growing or adult organisms suffering from insufficient or faulty ectoderm. Examples of diseases caused by damage to epidermal system cells include burn, wound, healing of wound, compression gangrene, psoriasis and the like. Examples of medical conditions which are alleviated by corneal transplantation include but are not limited to, scarring from infections, such as eye herpes or fungal keratitis, eye diseases such as keratoconus, hereditary factors or corneal failure from previous surgeries, thinning of the cornea and irregular shape (such as with keratoconus), complications from LASIK, chemical burns on the cornea or damage from an eye injury, excessive swelling (edema) on the cornea. Alternatively, the differentiated cells/tissue can be used in the treatment of medical conditions caused by damage to nervous system cells including, but not limited to, Alzheimer disease, Huntington chorea, Parkinson disease, ischemic cerebral disease, epilepsy, brain injury, vertebral injury, motor neuron disease, neurodegeneration disease, pigmentary retinal dystrophy, cochlear hearing loss, multiple sclerosis, amyotrophic lateral sclerosis, a disease due to a neurotoxin damage and the like.

The cells of the present invention can be administered to the treated subject using a variety of transplantation approaches, the nature of which depends on the site of implantation.

The term or phrase "transplantation", "cell replacement" "cell therapy" or "grafting" are used interchangeably herein and refer to the introduction of the cells of the present invention to target tissue.

Methods of administering the progenitor cells of the present invention to subjects, particularly human subjects include injection or implantation of the cells into target sites in the subjects, the cells of the invention can be inserted into a delivery device which facilitates introduction by, injection or implantation, of the cells into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The progenitor cells of the invention can be inserted into such a delivery device, e.g., a syringe, in different forms. For example, the cells can be suspended in a solution or embedded in a support matrix when contained in such a delivery device. As used herein, the term "solution" includes a carrier or diluent in which the cells of the invention remain viable. Carriers and diluents which can be used with this aspect of the present invention include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating progenitor cells as described herein in a carrier or diluent and, as required, other ingredients enumerated above, followed by filtered sterilization.

For transplanting, the cell suspension is drawn up into the syringe and administered to anesthetized transplantation recipients. Multiple injections may be made using this procedure.

The cellular suspension procedure thus permits grafting of the cells to any predetermined site e.g., in the skin, skull, gums, eye, brain or spinal cord. A relatively non-traumatic site, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

The cells may also be transplanted to a healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region. Whatever the case, following transplantation, the cells preferably migrate to the damaged area.

Since non-autologous cells are likely to induce an immune reaction when administered to the body, several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In any of the methods described herein, the cells can be administered either per se or, preferably as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

Suitable routes of administration include direct administration into the tissue or organ of interest. Thus, for example the cells may be administered directly into a specific region of the brain or to the spinal cord.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. For example, animal models of demyelinating diseases include shiverer (shi/shi, MBP deleted) mouse, MD rats (PLP deficiency), Jimpy mouse (PLP mutation), dog shaking pup (PLP mutation), twitcher mouse (galactosylceramidase defect, as in human Krabbe disease), trembler mouse (PMP-22 deficiency). Virus induced demyelination model comprise use if Theiler's virus and mouse hepatitis virus. Autoimmune EAE is a possible model for multiple sclerosis.

Animal models for neuronal diseases include 6-OHDA-lesioned mice which may be used as animal models of Parkinson's. In addition, a sunflower test may be used to test improvement in delicate motor function by challenging the animals to open sunflowers seeds during a particular time period.

Transgenic mice may be used as a model for Huntingdon's disease which comprise increased numbers of CAG repeats have intranuclear inclusions of huntingtin and ubiquitin in neurons of the striatum and cerebral cortex but not in the brain stem, thalamus, or spinal cord, matching closely the sites of neuronal cell loss in the disease.

Transgenic mice may be used as a model for ALS disease which comprise SOD-1 mutations.

The septohippocampal pathway, transected unilaterally by cutting the fimbria, mimics the cholinergic deficit of the septohippocampal pathway loss in Alzheimers disease. Accordingly animal models comprising this lesion may be used to test the cells of the present invention for treating Alzheimers.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1). For example, Parkinson's patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Support matrices in which the ectodermal progenitor cells can be incorporated or embedded include matrices which are recipient-compatible and which degrade into products which are not harmful to the recipient. Natural and/or synthetic biodegradable matrices are examples of such matrices. Natural biodegradable matrices include plasma clots, e.g., derived from a mammal, polymeric scaffolds, matrigel and collagen matrices. Synthetic biodegradable matrices (scaffolds) include synthetic polymers such as polyanhydrides, polyorthoesters, and polylactic acid. Other examples of synthetic polymers and methods of incorporating or embedding cells into these matrices are known in the art. See e.g., U.S. Pat. No. 4,298,002 and U.S. Pat. No. 5,308,701. These matrices provide support and protection for the fragile progenitor cells in vivo and are, therefore, the preferred form in which the ectodermal progenitor cells are introduced into the recipient subjects.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated Parkinson's patient will be administered with an amount of cells which is sufficient to alleviate the symptoms of the disease, based on the monitoring indications.

Generally, any method known in the art can be used to monitor success of transplantation. For example, MRI can be used for visualizing brain white matter and studying the burden of demyelinating lesions as currently practiced for monitoring MS patients. Magnetization transfer contrast can be used to monitor remyelination (Deloire-Grassin 2000 J. Neurol. Sci. 178:10-16). Magnetic resonance spectroscopy measurement of N-acetyl-aspartate levels can be used to assess impact on local neuron/axon survival. Using paramagnetic particles to label cells before transplantation enabling their dispersion to be tracked by MRI. Serial neurophysiology is useful for monitoring conduction. The optic nerve has particular advantages in this respect.

It will be appreciated that differentiating cultures or ectodermal tissues prepared from ectodermal progenitor cells of the present invention also provide a model suitable for the investigation of processes effecting ectoderm development and function. For example, the cells and tissues of the present invention may be cultured in the presence of suspected toxic materials, antibodies, teratogens, drugs, transgenes (e.g., expressing arious receptors, ligands, cell adhesion molecules, enzymes, peptide hormones and immune system proteins) and the like, or exposed to non-standard environmental factors such as temperature, gas partial pressure and pH, or co-cultured in the presence of cells from other tissues or other organisms. Changes in parameters of growth and development, such as failure or delay of ectodermal marker expression, loss of proliferative capacity, or dis-organization of ectoderm can be assessed to determine the effect of various factors.

Thus, according to another aspect of the present invention, there is provided a method of determining an effect of a factor on ectoderm development, growth and/or modification. The method is effected by exposing the population of ectodermal progenitor cells of the present invention to the factor, and determining an effect of the factor on the cells.

The ectodermal progenitor cells can be exposed to a factor suspected of inhibiting or downregulating ectoderm development, growth or differentiation. Such assays are well known in drug development and research, and may be employed to test undesirable side effects of substances intended for the treatment of other, non-ectodermal processes, or, alternatively, may be used to discover novel inhibitors of ectoderm formation. In order to enable assessment of effects inhibiting ectoderm development and growth, conditions of culturing the ectodermal progenitor cells should be favorable, or more preferably, optimal, for ectoderm formation. This includes optimization of medium components (such as growth or differentiation factors), temperature, substrate composition, gas partial pressures and the like, for the specific stage of ectoderm development being investigated.

Since progenitor cell populations are highly amenable to tissue engineering, transplantation and regenerative therapy, genetic manipulation of such cells can provide a source of developing cell populations bearing unique, previously unattainable characteristics.

The ectodermal progenitor cells of the present invention may be manipulated to express exogenous polypeptides by introduction of a nucleotide sequence encoding the exogenous polypeptide, or a precursor form of the exogenous polypeptide. Exogenous foreign nucleic acid sequences can be transferred to the ectodermal progenitor cells of the culture by electroporation, calcium phosphate, microinjection, lipofection, retro- or other viral or microbial vector or other means well known to one of ordinary skill in the art. Preferably, expression of the exogenous sequence(s) is inducible. Cells expressing the exogenous polypeptide may be screened and isolated by techniques well known in the art including, but not limited to, immunoblotting, immunofluorescence, ELISA and RT-PCR. Cells expressing exogenous polypeptides can be harvested, expanded, differentiated and used for, for example, repairing or augmenting a defect. In this manner, cells, tissues or organs can be prepared with exogenous major histocompatibility antigens which will decrease rejection of transplanted materials by the host organism. In addition, cells expressing and secreting neurotransmitters, or overexpressing growth factor receptors can be selected and cultured, creating cultures of ectodermal progenitor cells with altered temporal dynamics and/or sensitivities to differentiation factors.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND METHODS

Cell Culture—
Human ES cell lines (H9, I3, and I6) were cultured as described [11] on mitomycin-treated feeder layers of mouse embryonic fibroblasts (MEF) at 37° C. in 5% CO2. For differentiation, huES cells were cultured on 4% formaldehyde-fixed PA6 stromal cells in 85% Dulbecco's modified Eagle's medium (DMEM):Ham's F-12 medium (1:1) (Invitrogen, Carlsbad, Calif., http://wwwdotinvitrogendotcom), 15% Knockout Serum Replacement (Invitrogen), 1% nonessential amino acids (Invitrogen), 0.1 mM β mercaptoethanol (Invitrogen). At day 4, 0.5 nM human recombinant BMP-4 (R&D Systems Europe, Lille, France, http://wwwdotrndsystemsdotcom) was added for 3 days. At day 7, BMP-4 was removed, and cells were cultured in 90% DMEM:Ham's F12 medium (1:1), 10% fetal calf serum (FCII; HyClone, Logan, Utah, http://wwwdothyclonedotcom), 1% nonessential amino acids, and 0.1 mM β-mercaptoethanol (differentiation protocol 1) or in 60% DMEM, 30% Ham's F-12 medium, and 10% fetal calf serum (FCII; HyClone) supplemented with 5 μg/ml insulin, 0.5 μg/ml hydrocortisone, 50 μg/ml ascorbate, and 10 ng/ml recombinant human epidermal growth factor (IT1 medium; differentiation protocol 2) for 1 week. Different batches of fetal calf serum (HyClone) were tested, with similar results. Hela cells (human immortalized epithelial cell line derived from cervical cancer cells), HaCaT cells (human keratinocyte cell line), and MEF were cultured in DMEM with 10% fetal bovine serum (HyClone).

Teratoma Formation—
H9 or IT1 cells ($5\times10^6$ cells) were injected into the rear leg muscle of three or seven 4-week-old male SCID-beige mice, respectively. The three mice injected with H9 cells and three mice injected with IT1 cells were sacrificed after 10 weeks when tumors appeared in H9 injected mice. The four remaining mice were observed twice a week for 2 months for tumor appearance. The experiments were performed with the approval of the Committee for Animal Care and Use of the Faculty of Medicine at the Rappaport Institute of the Technion.

Antibodies and Immunofluorescence—
IT1 cells were fixed in ice-cooled methanol at 4° C. for 5 minutes and saturated with phosphate-buffered saline (PBS) containing 3% bovine serum albumin (Sigma-Aldrich, St. Louis, http://wwwdotsigmaaldrichdotcom) and 2% donkey serum for 30 minutes at room temperature. The cells were stained with primary antibodies for 60 minutes in saturation buffer, washed in PBS, and incubated with secondary antibodies for 40 minutes. Primary antibodies were as follows: mouse anti-K18 (Chemicon, Temecula, Calif., http://wwwdotchemicondotcom), rabbit anti-K14 (BabCo, Richmond, Calif., http://wwwdotbabcodotcom), and mouse anti-myc (Santa Cruz Biotechnology Inc., Santa Cruz, Calif., http://wwwdotscbtdotcom). Secondary fluorescent labeled donkey anti-rabbit or mouse IgG antibodies were purchased from Alexa Molecular Probes (Invitrogen, Cergy Pontoise, France, http://wwwdotinvitrogendotcom). For all studies, negative controls were performed by omitting the primary antibodies. The cell nuclei were stained with Hoechst 33342 bis-benzimide (Sigma-Aldrich). Mounted coverslips were analyzed under an Axiophot microscope with Neofluor objective lenses (Carl Zeiss, Oberkochen, Germany, http://wwwdotzeissdotcom). Images were acquired with a black and white Cohn camera piloted by the Qfish acquisition software (Leica, Heidelberg, Germany, http://wwwdotleicadotcom).

Vector Constructions and Lentiviral Transductions—
p63, pax-6, and tomato red fluorescent protein cDNA were amplified and cloned into 2K7bsd under the control of the human elongation factor (EFI) promoter, and lentiviral vector was produced as follows.

Viruses were produced in 293TFT cell culture. Briefly, T75 flasks were coated with sterile collagen diluted 1/50 (20 μg/ml) overnight at 37° C. then washed 3 times with sterile PBS. Fresh 293FT cells maintained in DMEM high-glucose supplemented with 10% FBS, 1 mM Non Essential AA, 1 mM Pyruvate (less than 20 passages) were used for virus production. One day prior to transfection, one T75 flask of 293FT (about 80% confluence) was split. Cells of 90% confluence were used and incubated with 10 ml fresh medium. 6 μg DNA was mixed with Opti-Mem medium (Invitrogen) incubated for 5 minutes. A lipofectamine mix was produced by mixing lipofectamine with Opti-Mem. Both mixtures were combined and added to the cells. Incubation lasted for over-night. Viruses were harvested from at least 48 hours post transfection. Virus concentration was effected on Centricon Plus 20, Millipore. The viruses were used for cell infection.

Three days after transduction, IT1 cells were harvested for further characterization.

Reverse Transcription-Polymerase Chain Reaction and Real-Time Quantitative Reverse Transcription-Polymerase Chain Reaction Analysis Total RNA was extracted using Trizol reagent (Invitrogen) and incubated with DNase I (Ambion, Austin, Tex. http://wwwdotambiondotcom) according to the manufacturer's instructions to destroy genomic DNA contamination. The cDNA was synthesized (1 µg of RNA per condition) using the PowerScript Reverse Transcriptase (Clontech, Saint-Germain-en-Laye, France, http://wwwdotclontechdotcom). The cDNA was analyzed by polymerase chain reaction (PCR) amplification using individual primer pairs for specific marker genes.

The following oligonucleotide primer sequences were used: oct-4 (GenBank Accession No. NM_203289, sense, 5'-gagaacaatgagaaccttcaggaga-3'; antisense, 5'-ttctggcgccg-gttacagaacca-3' SEQ ID NOs: 1 and 2, respectively), p63 (GenBank Accession No. AF075439 sense, 5'-gccacagtacac-gaacctgg-3'; antisense, 5'-tcgaaactgtgcgggcctggg-3' SEQ ID NOs: 3 and 4, respectively), lama3 (GenBank Accession No. Q99533, sense, 5'-catcgatgaccagcttctg-3'; antisense, 5'-catc-gatgaccagcttctg-3' SEQ ID NOs: 5 and 6, respectively), K18 (GenBank Accession No. NM_010664, sense, 5'-tagatgc-ccccaaatctca-3'; antisense, 5'-gtccaaggcatcaccaag-3' SEQ ID NOs: 7 and 8, respectively), and K14 (GenBank Accession No. AB101481, sense, 5'-atgattggcagcgtggag-3'; antisense, 5'-gtccagctgtgaagtgctt-3' SEQ ID NOs: 9 and 10, respectively).

The PCR products were then separated on 1.2% agarose gel and visualized by ethidium bromide fluorescence. For real-time quantitative PCR, the relative expression level of transcripts was quantified using the SYBR-Green PCR Master Mix on an ABI Prism 7700 Sequence Detection System (Applied Biosystems, Courtaboeuf, France, http://wwwdot-appliedbiosystemsdotcom) according to the manufacturer's instructions. Each reaction mixture contained a 300 nM concentration of each primer, and 5 µl of cDNA product diluted 1:25 was used. The amount of each gene relative to 36B4 internal control and the fold stimulation was calculated by using the equation $2^{-\Box\Box CT}$, where $\Box CT=CT$ gene–CT 36B4 and $\Box\Box CT\_=\_CT$ stimulated condition_-_CT unstimulated condition The results are the average of three separate experiments. The following primers were used: K14 (GenBank Accession No. AB101481, sense, 5'-gaccattgaggacctgagga-3'; antisense, 5'-catacttggtgcggaagtca-3', SEQ ID NOs: 11 and 12, respectively), glyceraldehyde-3-phosphate dehydrogenase (GenBank Accession No. NP_002037.2, sense, 5'-cca-catcgctcagacaccat-3; antisense, 5'-tgaccaggcgcccaat-3' SEQ ID NOs: 13 and 14, respectively), lama3 (GenBank Accession No. Q99533, sense, 5'-tgaagcccagcgcatga-3'; antisense, 5'-ccctttatcagcttctgctt-3', SEQ ID NOs: 15 and 16, respectively), 'Np63 (GenBank Accession No. AF075439, sense, 5'-tttcccaccccgagatga-3'; antisense, 5'-tgcggcgagcatccat-3', SEQ ID NOs: 17 and 18, respectively), and pax6 (GenBank Accession No. NM_011098, sense, 5'-acctggctagcgaaaag-caa-3; antisense, 5'-cccgttcaacatcctttagtttatca-3', SEQ ID NOs: 21 and 22, respectively).

Fluorescence-Activated Cell Sorting Analysis— huES cells were detached with PBS, 0.5% bovine serum albumin (BSA), 0.5 mM EDTA. For cellular staining, the cells were fixed in 2% formaldehyde in PBS; permeabilized in PBS, 0.5% saponin (Sigma-Aldrich), 0.5% BSA for 10 minutes; and saturated with PBS, 0.5% saponin, 0.5% BSA, 0.5% donkey serum for 30 minutes. Cells were stained with mouse anti-K14 (Novocastra Ltd., Newcastle upon Tyne, U.K., http://wwwdotnovocastra.co.uk) and with mouse anti-K18 (Chemicon). Donkey anti-mouse-coupled fluorescein isothiocyanate antibodies (Alexa Molecular Probes) were added for 45 minutes to reveal anti-K14 or anti-K18 staining. For human leukocyte antigen (HLA) expression, the detached cells were stained for 45 minutes with mouse anti-HLA class I-RPE or mouse anti-HLA class II-RPE (DakoCytomation, Trappes, France, http://wwwdotdakocytomationdotcom). Mouse isotype control monoclonal antibody (BD Pharmingen, San Diego, http://wwwdotbdbiosciences.com/index_us.shtml) and control donkey serum were used to set the background level of fluorescence. Cells were monitored by flow cytofluorometry on a FACScan system using CellQuest software (BD Biosciences, San Diego, http://wwwdotbdbiosciencesdotcom).

Karyotype—

Cell division was blocked in mitotic metaphase using colcemidspindle formation inhibitor (KaryoMax colcemid solution; Gibco, Grand Island, N.Y., http://wwwdotinvitrogendotcom). Nuclear membranes were broken after hypotonic treatment. For chromosome visualization, G-band standard staining (Giemsa; Merck & Co., Darmstadt, Germany, http://wwwdotmerckdotcom) was used as previously described [10]. The karyotypes were analyzed and reported according to the International System for Human Cytogenetic Nomenclature. At least 20 cells were examined from each sample.

RESULTS

Figure 4C:
Figure 4B:
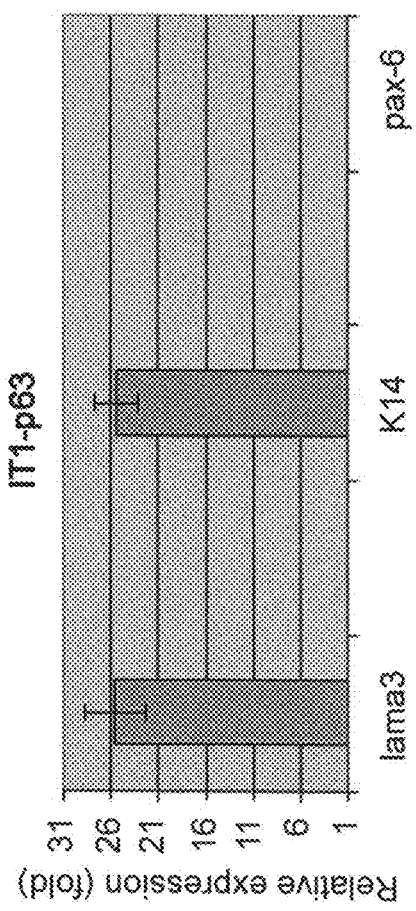

Human Embryonic Stem cells (hues) cells were seeded on formaldehyde-fixed PA6 stromal feeder cells in the absence of serum for 4 days and subjected to BMP-4 (0.5 nM) treatment for 3 days, followed by an additional 7 days of culturing in the presence of 10% fetal calf serum (FIG. 1A, protocol 1). Under these conditions, a large number of K18-positive ectodermal progenitor cells were produced (60%), along with K5/K14-positive keratinocytes (20%) (FIG. 1B). To isolate and amplify the huES-derived ectodermal K18 progenitors, the committed cells obtained at day 7 were grown on mouse embryonic fibroblast feeder in IT medium (60% DMEM+ 30% Ham-F12+10% FCS (FCII Hyclone)+5 □g/ml insulin+ 0.5 □g/ml hydrocortisone+10 ng/ml EGF) for an additional 7 days (FIG. 1A, protocol 2). Immunostaining and fluorescence-activated cell sorting analysis with K18 antibodies demonstrated that this procedure resulted in a homogeneous population of ectodermal cells, about 100% positive for K18 (FIGS. 1B, 1C). These cells, when grown on type I collagen and further cultivated for 15 passages, still remained homogenous for K8/K18 staining and proliferated. Thus, the sequential contribution of mesenchymal inducers (stromal feeders, BMP-4, and collagen) efficiently recapitulated in vitro the embryonic mesodermal stimulating effects on ectodermal cell fate. Like primary cells, this ES-derived ectodermal precursor population (which we refer to as IT1) entered senescence around passage 15, thus allowing an expansion up to 60 population doublings. IT1 cells showed a core of epithelial-shaped cells surrounded by cells with a more elongated morphology. This dimorphic aspect of the IT1 cells remained unchanged over the passages, even after the dilution cell cloning procedure (FIG. 2A). As illustrated by reverse transcription-PCR from total RNA, IT1 cells, as expected for ectodermal precursors, expressed K18 transcripts but not the keratinocyte-specific genes p63, K14, or lama3 and ceased to express Oct-4 (FIG. 2B). Embryonic stem cells are known to exhibit an unusual cell cycle profile, characterized by a truncated G1 phase and a high proportion of cells in S phase. As ES cells differentiate, their cell cycle structure becomes similar to that of somatic mammalian cells [13]. According to DNA content, IT1 exhibited a normal cell cycle (FIG. 2C) and a doubling time of 48 hours, longer than that required for their undifferentiated parental H9 cell line (36 hours). Cells recovered perfectly after cycles of cryopreservation and thawing, and their karyotype remained normal (FIG. 3A). As expected from the normal cell cycle profile and the absence of Oct-4 gene expression, subcutaneous injection of IT1 cells in nude mice, contrary to undifferentiated huES cells, did not produce teratoma even after more than 10 weeks (FIG. 3B). A recent study strongly suggested that the immunostimulatory capacity of differentiated huES is low compared with that of adult cells [14]. Analysis of major histocompatibility complex (MHC) class I and class II antigens showed a clear increase in HLA class I expression in IT1 as compared with ES cells, whereas MHC class II is undetectable in both cell lines (FIG. 3C). This feature suggests that IT1 may possess a degree of immune privilege, as already described for differentiated huES cells [14].

p63 is a member of the p53 family, which has been shown to be essential for the development of the epidermis and its derivative in vertebrates [15, 16]. Recently, it was demonstrated that the exogenous expression of _Np63 is necessary to differentiate murine K8/K18 ectodermal cells into K5/K14+ keratinocytes [17]. Accordingly, IT1 cells, transduced with a lentivirus expressing ΔNp63, became K14-positive cells (FIG. 4A, upper panels) de novo expressing keratinocyte-specific K14 and lama3 genes but not unrelated pax-6 gene as negative control (FIG. 4B). Infection of IT1 with control red tomato lentivector was unable to produce keratinocyte-like cells (FIG. 4A, lower panels). Moreover, the present inventors have also observed appearance of K14-positive cells when IT1 were seeded onto a keratinocyte-derived extracellular matrix, as visualized by immunofluorescence staining with K14+ specific antibodies (FIG. 4C).

In conclusion, the work described here demonstrates for the first time that a stable, somatic ectodermal cell population can be isolated from huES cells. The experimental procedure described here is simple and highly reproducible and does not require transgene expression for either cell sorting or antibiotic selection. It efficiently compensates for the absence of known cell-surface markers specific for the ectodermal lineage. The definite population doubling of IT1 cells, their normal cell cycle kinetics, and the absence of teratoma formation strongly suggest that although it is derived from huES cells, IT1 becomes a safe somatic cell population. The present inventors were also able to obtain ectodermal cell populations from two additional huES cell lines, I3 (IT2) and 16 (IT3), that were as homogenous as IT1. The IT1 cells described here will be particularly useful for designing in vitro models to recapitulate early events during embryonic epithelial lineage specification, as well as a source for committed, homogenous, nontumorigenic cell populations in clinical trials for epithelial stem cell loss.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited in the Document

1. Stern C D. Neural induction: 10 years on since the 'default model'. Curr; Opin Cell Biol 2006; 18:692-697.
2. Bagutti C, Hutter C, Chiquet-Ehrismann R et al. Dermal fibroblast derived growth factors restore the ability of beta (1) integrin-deficient embryonal stem cells to differentiate into keratinocytes. Dev Biol 2001; 231:321-333.
3. Coraux C, Hilmi C, Rouleau M et al. Reconstituted skin from murine embryonic stem cells. Curr Biol 2003; 13:849-853.
4. Kawasaki H, Mizuseki K, Nishikawa S et al. Induction of midbrain dopaminergic neurons from ES cells by stromal cell-derived inducing activity. Neuron 2000; 28:31-40.
5. Ji L, Allen-Hoffmann B L, de Pablo J J et al. Generation and differentiation of human embryonic stem cell-derived keratinocyte precursors. Tissue Eng 2006; 12:665-679.
6. Schuldiner M, Yanuka O, Itskovitz-Eldor J et al. Effects of eight growth factors on the differentiation of cells derived from human embryonic stem cells. Proc Natl Acad Sci USA 2000; 97:11307-11312.
7. Troy T C, Turksen K. Commitment of embryonic stem cells to an epidermal cell fate and differentiation in vitro. Dev Dyn 2005; 232: 293-300.
8. Gambaro K, Aberdam E, Virolle T et al. BMP-4 induces a Smad dependent apoptotic cell death of mouse embryonic stem cell-derived neural precursors. Cell Death Differ 2006; 13:1075-1087.
9. Green H, Easley K, Iuchi S et al. Marker succession during the development of keratinocytes from cultured human embryonic stem cells. Proc Natl Acad Sci USA 2003; 100:15625-15630.
10. Metallo C M, Ji L, de Pablo J J et al. Retinoic Acid and Bone Morphogenetic Protein Signaling Synergize to Efficiently Direct Epithelial Differentiation of Human Embryonic STEM CELLS 2007 [Epub ahead of print].
11. Amit M, Carpenter M K, Inokuma M S et al. Clonally derived human embryonic stem cell lines maintain pluripotency and proliferative potential for prolonged periods of culture. Dev Biol 2000; 227:271-278.
12. Suter D M, Cartier L, Bettiol E D et al. Rapid generation of stable transgenic embryonic stem cell lines using modular lentivectors. STEM CELLS 2006; 24:615-623.
13. White J, Dalton S. Cell cycle control of embryonic stem cells. Stem Cell Rev 2005; 1:131-138.
14. Drukker M, Katchman H, Katz G et al. Human embryonic stem cells and their differentiated derivatives are less susceptible to immune rejection than adult cells. STEM CELLS 2006; 24:221-229.

15 Mills A A, Zheng B, Wang X J et al. p63 is a p53 homologue required for limb and epidermal morphogenesis. Nature 1999; 398:708-713.
16 Yang A, Schweitzer R, Sun D et al. p63 is essential for regenerative proliferation in limb, craniofacial and epithelial development. Nature 1999; 398:714-718.
17 Aberdam D, Gambaro K, Rotagno P et al. Key role of p63 in BMP-4-induced epidermal commitment of embryonic stem cells. Cell Cycle 2007; 6:291-294.
18 Skottman H, Mikkola M, Lundin K et al. Gene expression signatures of seven individual human embryonic stem cell lines. STEM CELLS 2005; 23:1343-1356.

What is claimed is:

1. A method of producing a homogeneous population of human ectodermal progenitor cells, the method comprising:
   (a) culturing human ES cells on a first feeder layer which comprises stromal feeder cells in serum free medium comprising BMP-4 so as to obtain a heterogeneous population of cells comprising the human ectodermal progenitor cells;
   (b) culturing said heterogeneous population of cells in a medium comprising serum on a second feeder layer which comprises fibroblast feeder cells, wherein said first feeder layer and said second feeder layer are different to thereby produce the homogeneous population of human ectodermal progenitor cells which express K18 and which do not express K14.

2. The method of claim 1, wherein said stromal feeder layer is formaldehyde fixed.

3. The method of claim 1, wherein said step (a) is effected for about 7 days comprising:
   (i) culturing said human ES cells on said stromal feeder layer in said serum free medium from day 1 to day 4; and
   (ii) culturing said ES cells on said stromal feeder layer in said serum free medium in a presence of said BMP-4 from day 4 to day 7.

4. The method of claim 1, wherein step (b) is effected from day 7 to day 16.

5. The method of claim 1, wherein said homogenous population of human ectodermal progenitor cells comprises at least 95% of said ectodermal progenitor cells.

6. The method of claim 1, wherein said medium comprising serum further comprises epidermal growth factor.

7. The method of claim 1, wherein said medium comprising serum further comprises insulin, hydrocortisone, and/or ascorbate.

8. The method of claim 1, wherein said fibroblast feeder cells are Mitomycined feeder cells.

9. The method of claim 1, wherein said fibroblast feeder cells are embryonic fibroblasts or dermal fibroblasts.

* * * * *